United States Patent [19]

Novinson

[11] Patent Number: 4,804,779

[45] Date of Patent: Feb. 14, 1989

[54] CHEMICAL DETOXIFICATION OF POLYCHLORINATED BIPHENYLS (PCBS)

[75] Inventor: Thomas Novinson, Ventura, Calif.

[73] Assignee: The United States of America as represented by the Secretary of the Navy, Washington, D.C.

[21] Appl. No.: 794,928

[22] Filed: Nov. 4, 1985

[51] Int. Cl.$^4$ .............................................. C07C 51/16
[52] U.S. Cl. .................................................... 562/542
[58] Field of Search ........................................ 562/542

[56] References Cited

U.S. PATENT DOCUMENTS 3,444,095  5/1969  Thomas ............................... 562/542
3,565,919  2/1971  Friedrichses et al. .............. 562/542

*Primary Examiner*—Werren B. Lone
*Attorney, Agent, or Firm*—J. M. St. Amand

[57] ABSTRACT

The invention provides a two-step process where polychlorinated biphenyls (PCBs), i.e. biphenyl having 2 to 10 chlorine atoms, are first reduced to unsubstituted biphenyl, then oxidized to a biodegradable dicarboxylic acid having the formula: $(CH_2)_n (CO_2H)_2$, where n=0 to 10 possible —$CH_2$—units for application in aqueous systems including water, mud and wet soil.

2 Claims, No Drawings

CHEMICAL DETOXIFICATION OF POLYCHLORINATED BIPHENYLS (PCBS)

BACKGROUND OF THE INVENTION

The present invention relates to the chemical detoxification of polychlorinated biphenyls by converting them to non-hazardous substances. In particular, the invention relates to chemically destroying polychlorinated biphenyls on site for decontamination purposes without creating pollution or hazardous situations.

Polychlorinated biphenyls (PCBs) are chlorinated aromatics used as inert liquids for insulating power transformers, utility boxes, etc. PCBs are known to be carcinogenic and highly toxic in small quantities, when ingested, and for that reason, they are disposed of by burial in approved landfills. PCB spills from damaged utility boxes or during transfer and similar situations have created problems causing PCB contamination of the soil or areas where the spills occurred. This has necessitated the digging up and removal of soils and other materials, and transferring them to safe disposal sites for burial, but this does not detoxify the PCBs. Destruction of PCBs by combustion creates other hazards, since deadly airborne dioxins are produced if the combustion temperature is below 2500 degrees C.

Other methods for chemically reducing PCBs, such as by Raney nickel or cobalt catalysts, are unsatisfactory in that byproducts which may be hazardous to health and environment are produced. Reduction of PCBs by Raney nickel may leave nickel salts, which are known carcinogens, in the reaction medium. Other prior methods for chemically reducing PCBs do not dispose of biphenyl or polyphenylene, which is sticky, and non-biodegradable under ordinary conditions, and has sufficient toxicity to warrant still being a pollutant. Methods using sodium metal, sodium or potassium alloys, sodium hydride, and sodium amides are all impossible to use with water and aqueous systems, and, therefore, are hazardous for using to detoxify contaminated soils on site. Anhydrous conditions are rarely found at PCB spill sites.

Polychlorinated biphenyls (PCBs) are made by chlorinating biphenyl to obtain several isomers. The biphenyl, which has all positions occupied by hydrogen, is converted to polychlorinated biphenyl where 2 or more hydrogen atoms are replaced by chlorine, i.e. x=2 to 10 chlorines, depending upon the isomer, as shown below:

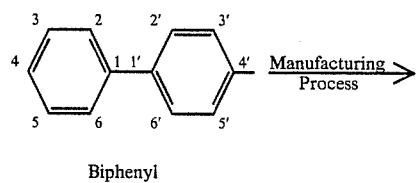

Biphenyl

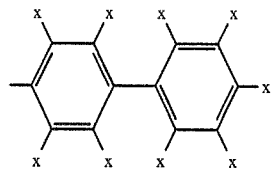

Polychlorinated Biphenyl

A two-step method has been sought which will convert PCBs directly into more easily handled, less toxic, more biodegradable, water or alkali soluble byproducts.

The present invention herein describes the reduction of the PCB isomers back to biphenyl, followed by oxidation to yield simpler, less toxic, more biodegradable organic carboxylic acids.

With the present invention a process is provided whereby PCBs can be chemically destroyed on site to detoxify contaminated soil and other areas. The process, as hereinafter described is useful in health, safety and pollution control since PCB contamination of water and soil is a major health and environment hazard.

SUMMARY OF THE INVENTION

Polychlorinated biphenyl is first converted to biphenyl by reduction using mild reducing agents and then further decomposed by oxidation to non-hazardous solids that are biodegradable and soluble in aqueous systems, as described in the equations:

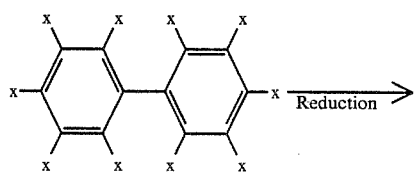

Polychlorinated Biphenyl where x = 2 to 10 Chlorine atoms

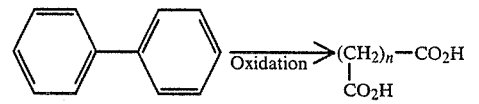

Biphenyl (all Chlorines are substituted by Hydrogen atoms)

where n = 1 to 10 units

DESCRIPTION OF THE PREFERRED EMBODIMENT

The invention provides a two-step process where polychlorinated biphenyls (PCBs), i.e. biphenyl having 2 to 10 chlorine atoms, are first reduced to unsubstituted biphenyl, then oxidized to a biodegradable dicarboxylic acid having the formula: $(CH_2)_n (CO_2H)_2$, where $n=0$ to 10 possible —$CH_2$— units for application in aqueous systems including water, mud and wet soil. The process effectively destroys PCBs by chemical catalysts and each step is best performed at a temperature range of from 25 to 80 degrees Centigrade.

Reduction of PCBs using a mild reducing agent that can be used in water or water alcohol systems, such as sodium borohydride in methanol/water, to yield biphenyl, followed by oxidation with potassium permanganate (or hydrogen peroxide or nitric acid) to yield benzoic acid or hexane-1,6-dicarboxylic acid, is a preferred method for detoxifying PCBs since both byproducts are biodegradable solids and relatively non-toxic compared to PCBs.

Raney nickel is less desirable because, as a catalst, it has to be recovered and reactivated with hydrogen, which is impractical for use in soil detoxification of PCBs. Nickel and nickel salts are suspect carcinogens. Besides, the catalyst is very pyrophoric and may ignite in air if improperly handled.

Other reducing agents, such as sodium or its alloys, sodium hydride, sodium amide, molten sodium, sodium amalgams, potassium or its alloys, lithium or its alloys, lithium aluminum hydride, etc., are stronger, but they react violently with water and so are impractical in detoxification of PCBs in soil.

Sodium, potassium, lithium, strontium, calcium, and magnesium borohydrides are mild reducing agents that can be used in alcohol and alcohol-water combinations. The byproducts, for reduction of PCBs with these agents, are innocuous sodium borate ("Borax") and sodium chloride.

Oxidizing agents that can oxidize biphenyl in alcohol (methanol, ethanol, isopropanol, etc.) or alcohol-water solutions without creating additional toxicity include, for example: permanganates (which yield manganese dioxide) of an alkali metal (i.e. sodium, potassium, cesium, rubidium, lithium) or alkaline earth metal (magnesium, strontium, calcium, but not barium or radium) or sodium or potassium persulfate (which leaves sodium or potassium sulfate), sodium or potassium perborate (which yields sodium borate known as "Borax", or potassium borate). Excluded are strong oxidizers such as osmium tetroxide, perchloric acid or its derivatives, thallium nitrate, and selenium dioxide, all of which are poisonous, but will work.

Examples of oxidizing agents that work in water or water-alcohol mixtures, and produce byproducts that have low toxicity are: permanganate salts —$NaMnO_4$, $KMnO_4$, $LiMnO_4$, $CsMnO_4$, $RbMnO_4$ (alkali derivatives) or $Ca(MnO_4)_2$, $Sr(MnO_4)_2$, and $Mg(MnO_4)_2$, but not $Ba(MnO_4)_2$ or $Ra(MnO_4)_2$; persulfate salts of —Na, K, Li, Rb or Cs or Ca, Mg, Sr, but not Ba or Ra; perborate salt of —Na, K, Li, Rb, Cs or Ca, Mg, Sr, but not Ba or Ra.

Reducing agents for PCBs that work in water or water-alcohol mixtures are: $NaBH_4$, $KBH_4$, $LiBH_4$, $Ca(BH_4)_2$, $Sr(BH_4)_2$, or $Mg(BH_4)_2$ (borohydride salts). As indicated previously, RNi (Raney nickel) catalyst will work, but is unsuitable because the material is a catalyst and has to be recovered and reactivated, is pyrophoric, and the metal and its salts are suspect carcinogens.

The final product of the two step chemical detoxification system for PCBs is a water soluble or alkali/water soluble (pH>7) mono- or dicarboxylic acid of the formula $HO_2C-(CH_2)_nCO_2H$ where n=1 to 10 —$CH_2$— units.

Byproducts of the reduction system are non-hazardous solids, i.e. $MnO_2$ from $NaMnO_4$, $KMnO_4$, etc. plus salts of $Na^+$, $K^+$, etc. or non-hazardous water soluble salts —$K_2SO_4$, $Na_2SO_4$, $Li_2SO_4$, $CaSO_4$, $MgSO_4$, $SrSO_4$ (sulfates from persulfate oxidizing salts), or from perborate —$NaBO_2$ or $Na_2B_4O_7$, $KBO_2$ or $K_2B_4O_7$, $LiBO_2$ or $Li_2B_4O_7$, $Ca(BO_2)_2$ or $CaB_4O_7$, $Mg(BO_2)_2$ or $MgB_4O_7$, and $Sr(BO_2)_2$ or $SrB_4O_7$.

The present system addresses both the reduction to biphenyl and oxidation to a water or alcohol-water soluble mixture that is biodegradable and soluble in aqueous systems. Prior systems based on potassium hydroxide or sodium hydroxide do not take care of the biphenyl or polyphenylene, which is sticky and non-biodegradable under ordinary conditions, and has sufficient toxicity to warrant being a pollutant. Methods based on sodium metal, sodium or potassium alloys, sodium hydride, or sodium amide are all impossible to use with water or aqueous systems.

Other modifications and variations of the present invention are possible in the light of the above teachings. It is therefore to be understood that within the scope of the appended claims the invention may be practiced otherwise than as specifically described.

What is claimed is:

1. A two-step process for chemically detoxifying polychlorinated biphenyl compounds to convert them to biodegradable and substantially harmless substances without the creation of hazardous byproducts or pollutants, comprising:
   (a) the first-step of reduction of polychlorinated biphenyl compounds at a temperature range of 25 to 80 degrees C. with a mild reducing agent selected from $NaBH_4$, $KBH_4$, $LiBH_4$, $Ca(BH_4)_2$, $Sr(BH_4)_2$, and $Mg(BH_4)_2$ that can safely be used in water or water-alcohol systems to yield unsubstituted biphenyl;
   (b) the second-step of oxidation of said unsubstituted biphenyl in a water or water-alcohol solution at a temperature range of 25 to 80 degrees C. using an oxidizing agent selected from: sodium or potassium persulfate, sodium or potassium perborate, and any permanganate of an alkali or alkaline earth metal which yields manganese dioxide with the exception of barium and radium permanganates to yield a biodegradable dicarboxylic acid having the formula: $(CH_2)_n(CO_2H)_2$ where n=1 to 10.

2. A two-step process for chemically detoxifying polychlorinated biphenyl compounds to convert them to biodegradable and substantially harmless substances without the creation of hazardous byproducts or pollutants, comprising:
   (a) the first-step of reducing polychlorinated biphenyl compounds with alkali or alkaline earth borohydrides (excluding radium and beryllium salts) in water-alcohol solution to produce a biphenyl or polyphenylene by-product, followed by
   (b) the second-step of oxidation of the biphenyl or polyphenylene by-product from the first-step with a permanganate, persulfate, or perborate salt of any alkali metal or alkaline earth metal (except radium or beryllium) in said water-alcohol solution to yield innocuous, low toxicity, water soluble carboxylic acid salts of said alkali or alkaline earth metals.

* * * * *